United States Patent [19]
Nagasaki et al.

[11] Patent Number: 5,892,136
[45] Date of Patent: Apr. 6, 1999

[54] PROCESS FOR PRODUCING IODOTRIFLUOROMETHANE

[75] Inventors: Noritaka Nagasaki; Nobumasa Suzuki; Satohiro Nakano; Nobuyuki Kunihiro, all of Yamaguchi, Japan

[73] Assignee: F-Tech Incorporated, Tokyo, Japan

[21] Appl. No.: 966,149

[22] Filed: Nov. 7, 1997

[30] Foreign Application Priority Data

Nov. 20, 1996 [JP] Japan .................................. 8-309260
Oct. 8, 1997 [JP] Japan .................................. 9-276186

[51] Int. Cl.$^6$ .................................................. C07C 19/07
[52] U.S. Cl. ............................................................ 570/174
[58] Field of Search .................................. 570/174, 243, 570/244, 245

[56] References Cited

U.S. PATENT DOCUMENTS 4,731,494  3/1988  Murib et al. ............................ 570/244

FOREIGN PATENT DOCUMENTS 608462  11/1960  Canada ................................... 570/174
0068110  6/1977  Japan ..................................... 570/174

*Primary Examiner*—Alan Siegel
*Attorney, Agent, or Firm*—McAulay Nissen Goldberg Kiel & Hand, LLP

[57] ABSTRACT

A novel process for producing iodotrifluoromethane is provided which comprises reacting trifluoromethane with iodine in the presence of oxygen by use of a catalyst containing a salt of a metal supported by a carbonaceous carrier. In this process, the catalyst life is lengthened greatly, the by-product is decreased, and the unreacted iodine can be recovered efficiently as high-purity iodine to be recycled without purification.

6 Claims, No Drawings

PROCESS FOR PRODUCING IODOTRIFLUOROMETHANE

BACKGROUND OF THE INVENTION

1. Field of the Invention

The present invention relates to a process for producing iodotrifluoromethane. More specifically, the present invention relates to a process for producing iodotrifluoromethane by reacting trifluoromethane with iodine in the presence of oxygen by use of a catalyst comprising a metal salt supported on a carbonaceous carrier.

2. Description of the Related Art

Iodotrifluoromethane is not only promising as a fire extinguisher substituting for Halon 1301 and Halon 1211, but also highly useful as a fluorine-containing intermediate compound for introducing a trifluoromethyl group in production of surfactants, agricultural chemicals, pharmaceuticals, and the like. Halon 1301, Halon 1211, and the like conventional fire extinguishers destroy the ozone layer, or cause global temperature rise by a greenhouse effect. Use of such extinguishers are being prohibited by environmental protection laws. On the other hand, the iodotrifluoromethane, which has a significantly shorter life in the air, causes negligibly the ozone layer destruction and the global temperature elevation. Therefore, the iodotrifluoromethane is promising for use as the fire extinguisher.

Several processes are known for production of iodotrifluoromethane. For example, J. Chem. Soc. 1951 p.584, and J. Org. Chem. 1967 p.833 disclose processes of reacting an alkali metal trifluoroacetate or silver trifluoroacetate with iodine; and J. Org. Chem. 1958 p.2016, and JP-A-2-262529 disclose processes of reacting a trifluoroacetyl halide with potassium iodide or lithium iodide.

Any of the above known methods employs expensive trifluoroacetic acid or its derivative as the source material. Moreover, use of alkali trifluoroacetate as the source material requires complete elimination of water including water of crystallization from the reaction system, and yet the yield is as low as about 70%. The expensive silver trifluoroacetate, although it gives a higher yield, is not necessarily advantageous to an industrial process.

JP-A-52-68110 discloses a process for producing iodotrifluoromethane in which trifluoromethane is reacted with iodine in the presence of a catalyst comprising an alkali metal salt or an alkaline earth metal salt supported by active carbon or active alumina. This process was replicated carefully by the inventors of the present invention. Consequently, it was found that, in the disclosed process, carbon deposition occurs, lowering significantly the catalyst activity in one or two days of the reaction, and the recovered iodine contains significant amount of a paste-like impurity estimated to be a high polymer. This recovered iodine cannot readily be purified, and complicated equipment is required for purification of the recovered iodine for recycling. Therefore, this process is not applicable to an industrial production.

As described above, the disclosed processes of production of iodotrifluoromethane from trifluoroacetic acid or its derivative are disadvantageous in that the source material is expensive, and use of more expensive silver salt of the trifluoroacetic acid is required for improving the yield. The conventional process of production of iodotrifluoromethane from trifluoromethane is also disadvantageous in that the catalyst life is short owing to carbon deposition, and the process requires a complicated equipment for eliminating a large amount of paste-like impurity from the recovered iodine for recycling it.

Therefore, a novel process for producing iodotrifluoromethane is demanded to overcome the disadvantages.

Under such circumstances, the inventors of the present invention made comprehensive studies on the process for producing iodotrifluoromethane by reaction of trifluoromethane with iodine. As the results, it was found that the reaction of trifluoromethane with iodine can be conducted with a long catalyst life in the presence of a catalyst comprising a metal salt supported on a carbonaceous carrier with coexistence of oxygen, and that the iodine which has not been converted to iodotrifluoromethane and by-product iodopentafluoroethane is recovered in a high purity without a paste-like impurity at a high recovery ratio and can be recycled without purification. The present invention is accomplished on the basis of the above findings.

SUMMARY OF THE INVENTION

The present invention intends to provide a process for producing iodotrifluoromethane applicable to industrial production with less amount of by-products at a low cost.

The process for producing iodotrifluoromethane of the present invention comprises reacting trifluoromethane with iodine in the presence of oxygen by use of a catalyst containing a metal salt supported on a carbonaceous carrier.

DETAILED DESCRIPTION OF THE PREFERRED EMBODIMENT

The catalyst system comprising a metal salt supported by a carbonaceous carrier according to the present invention exhibits high performance, retaining high activity for a long term and giving high conversion and high selectivity. The coexistence of oxygen with the catalyst of the present invention enables efficient production of iodotrifluoromethane by simple reaction of trifluoromethane with iodine. In the present invention, the iodine fed to the reaction system is converted to the iodotrifluoromethane and by-product iodopentafluoroethane, and the unreacted iodine is recovered as high-purity iodine by simple cooling of the reaction mixture.

The present invention is described below more specifically.

The catalyst employed in the present invention is a metal salt supported by a carbonaceous carrier.

The carbonaceous carrier in the present invention includes active carbon, graphite, fibrous active carbon, and carbon molecular sieves.

The carbonaceous carrier may be a mixture of the above carbonaceous materials, if necessary. The carbonaceous carrier is preferably in a shape of powder, particles, lumps, or the like, preferably in a shape of spheres, columns, tablets, or particles in a size ranging from about 2 to about 15 mm, but is not limited thereto.

The carbonaceous carrier may be treated by nitric acid, hydrochloric acid, phosphorus acid, or the like for eliminating impurities such as ash, if necessary.

Incidentally, alumina, silica, and titania, which are employed generally as the catalyst carrier, are not preferred since they will give low activity of the catalyst in forming iodotrifluoromethane or they can be decomposed under the reaction conditions of the present invention.

The metal for the catalyst of the present invention includes an alkali metal and/or an alkaline earth metal; and combinations of an alkali metal and a noble metal, an alkaline earth metal and a noble metal, and an alkali metal, an alkaline earth metal and a noble metal.

The alkali metal includes lithium, sodium, potassium, rubidium, and cesium. Of these, potassium, rubidium, and cesium are preferred. The metals may be used singly or in combination. More preferably, a combination of potassium and cesium, or potassium and rubidium is used.

The alkaline earth metal includes beryllium, magnesium, calcium, strontium, and barium. Of these, magnesium, calcium, barium, and/or mixtures thereof are preferred. The alkaline earth metal may be used in combination with an alkali metal. A combination of alkali metal and magnesium as the alkaline earth metal is particularly preferred.

The noble metal employed in the present invention includes platinum, ruthenium, rhodium, palladium, and iridium. These noble metals may be used singly or in combination. Of these noble metals, platinum and rhodium are preferred. The noble metal may be used in combination with an alkali metal, with an alkaline earth metal, or with an alkali metal and an alkaline earth metal. Of the combinations of the metals, preferred are combinations of an alkali metal with a noble metal, more preferred are a combination of potassium, cesium, and platinum; and a combination of potassium, rubidium, and platinum.

The metal is supported, in the present invention, as a salt on a carbonaceous carrier. The salt of the alkali metal, the alkaline earth metal, or the noble metal is usually selected from metal salt-forming substances such as hydroxides, halides, nitrates, carbonates, carboxylates, alkoxides, and the like in consideration of the solubility in the solvent, the ease of handling, commercial availability as the reagent, the stability, the behavior in the drying process and the thermal decomposition process.

The method of depositing the above metal salt onto the carbonaceous carrier is not specially limited in the present invention. The salt may be deposited by a conventional method for preparing a supported catalyst such as an impregnation method, a precipitation method, and a kneading method. Of these deposition methods, the impregnation method is preferred in consideration of the simplicity of the process and production cost.

The impregnation method may be conducted, for example, as follows. Firstly, a prescribed amount of the metal salt is dissolved in a solvent at room temperature or, if necessary, at an elevated temperature. The solvent may be selected from water, organic solvents, and mixtures thereof. The organic solvents include alcohols, ketones, ethers, and aromatic compounds. Of these solvents, water, methanol, and acetone are preferred in consideration of the cost and the safety. The amount of the solvent to be used depends largely on the kinds of the carbonaceous carrier, the metal salt, and the solvent, and cannot specially be limited. For example, when active carbon is used as the carrier, the solvent is used suitably in an amount ranging from 50 to 1000 mL for 100 g of the active carbon. Secondly, in the impregnation method, a prescribed amount of the carbonaceous carrier is immersed into the solution containing a metal salt. The immersion is continued for two hours or longer, overnight standing being acceptable. If the whole of the solution has been absorbed during the immersion, the carrier is directly dried preliminarily in a conventional drier at a temperature from 80° to 150° C. If some of the solution remains unabsorbed, the solvent is evaporated in a flask on a water bath, or by a rotary evaporator with gradual pressure reduction, and then the carrier is preliminarily dried as above by a drier. In the case where two or more kinds of salts selected from alkali metals and alkaline earth metals are deposited, the metal salts may be dissolved in one and the same solvent and are deposited simultaneously in a manner described above. On the other hand, in the case where an alkali metal and/or an alkaline earth metal, and a noble metal is deposited, preferably the deposition is conducted separately in succession, more preferably the noble metal firstly and the alkali metal and/or the alkaline earth metal subsequently, in the present invention.

After the deposition of the metal salt onto the carbonaceous carrier, the carrier is further dried and calcined before use as the catalyst in the present invention. The drying and the calcination may be conducted either in separate steps or in one step. The conditions for the drying and the calcination depend largely on the metal, the carrier, and the deposition method, and cannot specially be limited. For example, for the drying and the calcination, the preliminarily dried metal-supporting carrier is filled into a reaction tube, dried at 100°–200° C. for 1–3 hours with introduction of an inert gas like nitrogen or argon, and then calcined at 400°–750° C. for 1–5 hours. The calcination at the temperature above 750° C. is liable to cause undesired aggregation or evaporation of the metal salt to cause drop of the catalyst activity disadvantageously.

The amount of the metal deposited on the carbonaceous carrier ranges from 0.1% to 50% by weight of the entire catalyst weight in the present invention. At the amount of less than 0.1% by weight, sufficient catalyst activity cannot be achieved, whereas at the amount of more than 50% by weight, the excess metal is not effective in improving the catalyst activity.

The atomic ratio of the noble metal to the alkali metal and/or alkaline earth metal ranges from 0.001 to 1.0 in the present invention. At the ratio of lower than 0.001, the effect of the noble metal for lengthening the catalyst life is little, whereas at the ratio of higher than 1.0, the catalyst cost is high owing to the expensiveness of the noble metal, undesirably.

The source materials employed in the present invention are trifluoromethane, iodine, and oxygen. The purity of the trifluoromethane is not specially limited, but is preferably not lower than 97%. The iodine may be a commercial product. The oxygen may be pure oxygen, or air. The oxygen may be diluted, if necessary, with an inert gas such as nitrogen, helium, and argon.

The style or method of the reaction process is not specially limited. The reaction may be conducted in a reactor of a fixed bed type, a fluidized bed type, or a moving bed type in the present invention. From the simplicity of the production process, the fixed bed is preferred. The reaction with the fixed bed type reactor is conducted, for example, as below. A gaseous mixture of the source materials are fed continuously to the reactor filled with the catalyst prepared as above and maintained at a prescribed reaction temperature. In formation of the gas mixture, the iodine which is solid ordinarily is melted by heating, and into the molten iodine, gaseous trifluoromethane is introduced in bubbles to form a gaseous mixture of trifluoromethane and iodine. Thereto oxygen is added. Thus the prescribed amount of iodine can be fed to the reaction system.

The molar ratio of the iodine to the trifluoromethane employed in the present invention ranges from 0.05 to 10, preferably from 0.05 to 3. At the molar ratio lower than 0.05, the selectivity is low, whereas at the molar ratio of higher than 10, the unreacted iodine to be recovered increases, which is disadvantageous industrially.

The volume ratio of the oxygen to the trifluoromethane employed in the present invention ranges from 0.01 to 1.0. At the volume ratio lower than 0.01, the catalyst activity deteriorates remarkably rapidly to shorten the catalyst life, and the purity of the solid iodine separated after the reaction is lower. On the other hand, at the molar ratio higher than 1.0, the carbonaceous carrier of the catalyst tends to burn disadvantageously.

The reaction temperature in the present invention ranges from 300° to 750° C., preferably from 400° to 600° C. At the reaction temperature lower than 300° C., the reaction velocity is extremely low, whereas at the reaction temperature higher than 750° C., decomposition of the formed iodotrifluoromethane occurs disadvantageously.

The reaction pressure in the present invention is not specially limited, but the pressure is not lower than atmospheric pressure and is not higher than 2 MPa in consideration of the properties of the source materials and the formed products.

The construction material for the reaction apparatus includes carbon steel, cast iron, stainless steel, copper, nickel, and Hastelloy. However, carbon steel, cast iron, stainless steel, copper, and nickel can be corroded to cause scale formation. Therefore, Hastelloy is preferred as the construction material for the reaction tube and related apparatus exposed to the reaction temperature in the present invention.

In the process of the present invention, the reaction gas mixture discharged from the reaction tube is cooled, and is separated into a gas and a solid. The gas is distilled under pressure in a conventional manner to separate the formed iodotrifluoromethane from the unreacted trifluoromethane. The unreacted trifluoromethane is recovered and recycled to the reaction system. The iodotrifluoromethane is the intended final product. The distillation may be conducted either by a batch system or a continuous system. On the other hand, the separated solid is unreacted iodine. The unreacted iodine herein means the iodine which has not been converted to the intended iodotrifluoromethane or the by-products such as iodopentafluoroethane. It is characteristic to the present invention that the unreacted iodine can be recovered efficiently as high-purity iodine, and the recovered iodine can be recycled directly without purification. Industrially, the iodine is recovered by a gas-solid separation column equipped with a scraper, and the recovered iodine can be recycled directly to the iodine evaporator, requiring no troublesome purification process. Therefore, the process is simple and economical.

On the other hand, in the absence of the oxygen, or with a non-carbonaceous carrier, the recovered iodine contains the paste-like impurity estimated to be a high polymer in a large amount. The recovery of the iodine was tried by distillation or sublimation. Thereby, it was found that the iodine recovery ratio is as low as about 73% to about 80% owing to the paste-like impurity, and the recycling of the recovered iodine without purification to the reaction system resulting in remarkable drop in the conversion of trifluoromethane, the selectivity and yield of iodotrifluoromethane.

The present invention is described more specifically by reference to examples without limiting the invention.

For simplicity, the source materials and the products are abbreviated as shown below:

Trifluoromethane: $CHF_3$
Oxygen: $O_2$
Iodine : $I_2$
Iodotrifluoromethane: $CF_3I$
Iodopentafluoroethane: $C_2F_5I$
Tetrafluoromethane : $CF_4$ The conversion ratio, and the selectivity shown in the examples are defined as below.

Conversion ratio (%)
=[(Moles of converted $CHF_3$)/(Moles of fed $CHF_3$)]×100
Selectivity (%)
=[(Moles of product)/(Moles of converted $CHF_3$)]×100

EXAMPLE 1

[Catalyst Preparation]
(1) Preparation of Catalyst Supported by Active Carbon:
 (a) A prescribed amount of a noble metal salt was dissolved in 400 g of water. Thereto, 300 g of active carbon was added, and immersed overnight. The noble metal salt solution was entirely absorbed by the active carbon without leaving an unabsorbed solution. This active carbon was transferred to a vat, and was preliminarily dried in a drier at a temperature of 90° to 110° C. for 6 hours.
 (b) A prescribed amount of an alkali metal salt and/or an alkaline earth metal salt was dissolved in 400 g of water. Thereto, the active carbon treated in the above step (a) was added, and immersed overnight. After the immersion, a small amount of the solution of the alkali metal salt and/or the alkaline earth metal salt remained unabsorbed. This mixture was treated by a rotary evaporator with gradual pressure reduction to remove water.
 (c) The active carbon was transferred to a vat, and dried preliminarily in a drier at a temperature of from 90° to 110° C. for 6 hours. The preliminarily dried active carbon was transferred to a heating furnace, and further, under a nitrogen stream, dried at 150° C. for one hour and calcined at 550° C. for one hour to obtain a catalyst.

A catalyst containing no noble metal salt was prepared by conducting the above steps (b) and (c) without conducting the step (a).
(2) Preparation of Catalyst Supported on Graphite or Carbon Molecular Sieve:

The catalyst was prepared in the same manner as the above steps (1)-(b) and (1)-(c).
(3) Preparation of Catalyst Supported on Active Alumina, Silica, or Titania:

The catalyst was prepared in the same manner as in the preparation (2) above.

The metal salts were commercial reagents. The carbonaceous carriers employed were as shown below.

Active Carbon: Shirasagi C2
 (Takeda Chemical Industries, Ltd.)
Graphite: Press-molded product of graphite powder
 (Wako Pure Chemical Industries, Ltd.)
Carbon Molecular Sieve: Molsievon
 (Takeda Chemical Industries, Ltd.)
Active Alumina: KHS-46 (Sumitomo Chemical Co. Ltd.)
Silica: CARiACT-Q-50 (Fuji Silicia K.K.)
Titania: CS-300-24 (Sakai Kagaku K.K.)

Table 1 shows the prepared catalysts and the amounts of the supported metals.

EXAMPLES 2–5

Into a reaction tube of inside diameter of 25 mm made from Hastelloy C, was filled 100 mL of Catalyst A, B, C, or D prepared in Example 1. The reaction tube was heated, and a gas mixture composed of $CHF_3$, $I_2$, and $O_2$ was fed into the reaction tube at the feed rate at the reaction temperature shown in Table 2. The gas after the reaction was cooled by passing a cooling tube to separate a solid matter from the gas. The gas was analyzed by gas chromatography. Table 3 shows the results of analysis of the reaction gases after lapse of the prescribed times from the start of the reaction. The solid matter separated from the reaction gas by cooling was a blackish violet plate- shaped crystalline matter having metallic luster in any of Examples 2–5. The recovered solids contained respectively iodine at a content of not lower than 98% by analysis of iodine according to JIS K8920.

Table 3 shows that the catalysts comprising the alkali metal salt and the noble metal salt, or the alkali metal salt, the alkaline earth metal salt and the noble metal salt, supported by active carbon had high activity, high selectivity, and long life.

EXAMPLES 6–8

The reaction was conducted with Catalyst E, F, or G prepared in Example 1 under the conditions shown in Table 2. The results are shown in Table 3. The solid matter separated from the reaction gas by cooling was a blackish violet plate-shaped crystalline matter having metallic luster in any of Examples 6–8. The recovered solids contained respectively iodine at a content of not lower than 98% by analysis of iodine in the same manner as in Examples 2–5.

Table 3 shows that the catalysts comprising the alkali metal salt, the alkaline earth metal salt and the noble metal supported by active carbon exhibited high activity, high selectivity, and a long life.

EXAMPLES 9–12

The reaction was conducted with Catalyst H, I, J, or K prepared in Example 1 under the conditions shown in Table 2. The results are shown in Table 3. The solid matter separated from the reaction gas by cooling was a blackish violet plate-shaped crystalline matter having metallic luster in any of Examples 9–12. The recovered solids contained respectively iodine at a content of not lower than 98% by analysis of iodine in the same manner as in Examples 2–5.

Table 3 shows that, of the the alkali metal salts supported on active carbon, the potassium salt catalyst exhibited high selectivity, and the cesium salt catalyst exhibited high activity, while the alkaline earth metal salt catalysts had low activity.

EXAMPLES 13

The reaction was conducted with Catalyst F prepared in Example 1 and by use of air instead of oxygen under the conditions shown in Table 2. The results are shown in Table 3. The solid matter separated from the reaction gas by cooling was a blackish violet plate-shaped crystalline matter having metallic luster. The recovered solids contained iodine at a content of not lower than 98% by analysis of iodine in the same manner as in Examples 2–5.

EXAMPLE 14–16

The reaction was conducted with Catalyst L (graphite), M (graphite), or N (carbon molecular sieve) prepared in Example 1 under the conditions shown in Table 2. The results are shown in Table 3. Any of the solid matters separated from the reaction gas by cooling was a blackish violet plate-shaped crystalline matter having metallic luster in any of Examples 14–16. The recovered solids contained respectively iodine at a content of not lower than 98% by analysis of iodine in the same manner as in Examples 2–5.

EXAMPLES 17–18

The reaction was conducted in the same manner as in Example 2 except that the black plate-shaped iodine having metallic luster recovered in Example 2 or Example 4 was used without treatment as the iodine source material. The results were nearly the same as in Example 2.

Comparative Examples 1–4

The reaction was conducted with Catalyst E, F, or H (active carbon), or M (graphite) prepared in Example 1 without addition of oxygen under the conditions shown in Table 2. The results are shown in Table 3. The catalyst life was significantly short in the absence of oxygen. The solid matter separated from the reaction gas contained a paste-like impurity estimated to be a high polymer. The recovery of the iodine therefrom by distillation or sublimation was particularly difficult. The solid matter contained iodine at a content of 72% to 85% in any of the Comparative Examples 1–4.

Comparative Example 5

The reaction was conducted with Catalyst O (active alumina) prepared in Example 1 without addition of oxygen under the conditions shown in Table 2. The results are shown in Table 3. The intended reaction did not proceed with the catalyst employing active alumina as the carrier.

Comparative Examples 6–8

The reaction was conducted with Catalyst O (active alumina), P (silica), or Q (titania) prepared in Example 1 under the conditions shown in Table 2. The results are shown in Table 3. The intended reaction did not proceed with the catalyst supported by the carrier other than the carbonaceous carrier even with coexistence of oxygen. The solid matter separated from the reaction gas was a blackish brown muddy solid and not readily scraped out from the gas-solid separator in any of Comparative Examples 6–8. The iodine content in the solid matter was in the range of 85% to 93% as measured in the same manner as in Examples 2–5.

Comparative Example 9

The reaction was conducted in the same manner as in Comparative Example 1. After 50 hours from the start of the reaction, the feed of $CHF_3$ and $I_2$ was stopped with the reaction conditions kept unchanged, and nitrogen (120 mL/min) and oxygen (8 mL/min) were fed in place of $CHF_3$ and $I_2$ for 5 hours to the reactor for the purpose of reactivation of the catalyst. Thereafter, $CHF_3$ and $I_2$ were fed under the conditions of Comparative Example 1 for the reaction. However, the catalyst activity was not restored by the above reactivation operation.

In production of iodotrifluoromethane by reaction of trifluoromethane and iodine according to the present invention, the catalyst has remarkably long life with the catalyst activity and the selectivity retained by conducting the reaction in the presence of oxygen with a catalyst comprising a metal salt supported by a carbonaceous carrier. In this process, the unreacted iodine which has not been converted to iodotrifluoromethane or iodopentafluoroethane can be recovered entirely as high-purity iodine, and be recycled without purification. Thus, the present invention provides a low-cost simple process for producing iodotrifluoromethane in comparison with conventional processes which employ expensive trifluoroacetic acid or its derivative as the source material, and is highly useful industrially.

TABLE 1

| Catalyst | Carrier | Supported component | Amount of metal supported (wt %) |
|---|---|---|---|
| A | Active carbon | $KNO_3$ | 1.7 |
|   |   | $CsNO_3$ | 5.8 |
|   |   | $H_2PtCl_6$ | 0.5 |
| B | Active carbon | $KNO_3$ | 2.35 |
|   |   | $RbNO_3$ | 5.15 |
|   |   | $H_2PtCl_6$ | 0.5 |
| C | Active carbon | $KNO_3$ | 6.7 |
|   |   | $Mg(NO_3)_2$ | 0.8 |
|   |   | $H_2PtCl_6$ | 1.0 |
| D | Active carbon | $KNO_3$ | 7.5 |
|   |   | $H_2PtCl_6$ | 1.0 |
| E | Active carbon | $KNO_3$ | 1.7 |
|   |   | $CsNO_3$ | 5.8 |
| F | Active carbon | $KNO_3$ | 2.35 |
|   |   | $RbNO_3$ | 5.15 |
| G | Active carbon | $KNO_3$ | 6.7 |
|   |   | $Mg(NO_3)_2$ | 0.8 |
| H | Active carbon | $KF$ | 7.5 |
| I | Active carbon | $CsCl$ | 7.5 |
| J | Active carbon | $Mg(NO_3)_2$ | 7.5 |
| K | Active carbon | $Ba(NO_3)_2$ | 7.5 |
| L | Graphite | $KNO_3$ | 2.35 |
|   |   | $RbNO_3$ | 5.15 |
| M | Graphite | $RbNO_3$ | 7.0 |
|   |   | $Mg(NO_3)_2$ | 0.5 |
| N | Carbon molecular sieve | $KNO_3$ | 1.7 |
|   |   | $RbNO_3$ | 2.1 |
|   |   | $Mg(NO_3)_2$ | 0.4 |
| O | Active alumina | $KNO_3$ | 1.7 |
|   |   | $CsNO_3$ | 5.8 |
|   |   | $H_2PtCl_6$ | 0.5 |
| P | Silica | $KF$ | 7.5 |
| Q | Titania | $KF$ | 7.5 |

TABLE 2

| | Reaction temperature (°C.) | $CHF_3$ (mL/min) | $I_2$ (mL/min) | $O_2$ (mL/min) | Air (mL/min) | $I_2/CHF_3$ (molar ratio) | $O_2/CHF_3$ (volume ratio) |
|---|---|---|---|---|---|---|---|
| Example | | | | | | | |
| 2–4 | 550 | 80 | 40 | 8 | — | 0.5 | 0.1 |
| 5 | 475 | 80 | 24 | 16 | — | 0.3 | 0.2 |
| 6–8 | 550 | 80 | 40 | 8 | — | 0.5 | 0.1 |
| 9 | 475 | 80 | 24 | 16 | — | 0.3 | 0.2 |
| 10–12 | 550 | 80 | 40 | 8 | — | 0.5 | 0.1 |
| 13 | 550 | 80 | 24 | — | 80 | 0.3 | 0.2 |
| 14–16 | 550 | 20 | 20 | 2 | — | 1.0 | 0.1 |
| Comparative example | | | | | | | |
| 1–2 | 550 | 80 | 40 | — | — | 0.5 | — |
| 3 | 475 | 80 | 24 | — | — | 0.3 | — |
| 4 | 550 | 20 | 20 | — | — | 1.0 | — |
| 5 | 550 | 20 | 20 | — | — | 1.0 | — |
| 6–8 | 550 | 20 | 20 | 2 | — | 1.0 | 0.1 |

TABLE 3

| | Catalyst | Reaction time lapse (min) | $CHF_3$ Conversion (%) | Selectivity (%) | | | $CF_3I$ Yield (%) |
|---|---|---|---|---|---|---|---|
| | | | | $CF_3I$ | $CF_4$ | $C_2F_5I$ | |
| Example | | | | | | | |
| 2 | A | 10 | 73.2 | 38.3 | 5.0 | 2.1 | 28.0 |
|   |   | 250 | 72.1 | 39.5 | 4.6 | 1.9 | 28.5 |
|   |   | 600 | 70.9 | 40.1 | 3.9 | 1.6 | 28.4 |
| 3 | C | 10 | 63.2 | 48.2 | 5.2 | 2.4 | 30.5 |
|   |   | 250 | 62.7 | 48.6 | 4.9 | 2.3 | 30.5 |
|   |   | 600 | 60.9 | 49.2 | 4.4 | 2.2 | 30.0 |
| 4 | D | 10 | 48.9 | 40.1 | 3.5 | 2.6 | 19.6 |
|   |   | 250 | 48.6 | 41.2 | 3.3 | 2.7 | 20.0 |
|   |   | 600 | 47.2 | 42.6 | 3.1 | 2.5 | 20.1 |
| 5 | B | 10 | 46.8 | 65.7 | 2.0 | 1.7 | 30.7 |
|   |   | 250 | 45.1 | 65.5 | 1.9 | 1.6 | 29.5 |
|   |   | 600 | 44.9 | 65.6 | 1.5 | 1.6 | 29.5 |
| 6 | E | 10 | 72.4 | 38.1 | 8.1 | 1.9 | 27.6 |
|   |   | 30 | 72.2 | 38.1 | 7.9 | 1.8 | 27.5 |
|   |   | 50 | 72.1 | 38.3 | 7.6 | 1.8 | 27.6 |
|   |   | 250 | 71.9 | 38.4 | 6.5 | 1.6 | 27.6 |
|   |   | 600 | 32.4 | 53.9 | 2.6 | 1.3 | 17.5 |
| 7 | G | 10 | 62.5 | 48.1 | 5.9 | 3.1 | 30.1 |
|   |   | 250 | 61.4 | 48.4 | 5.7 | 3.0 | 29.7 |
|   |   | 600 | 25.7 | 54.5 | 2.1 | 1.8 | 14.0 |
| 8 | F | 10 | 45.1 | 65.9 | 2.1 | 1.6 | 29.7 |
|   |   | 30 | 45.1 | 65.9 | 2.0 | 1.5 | 29.7 |
|   |   | 50 | 44.8 | 65.7 | 2.0 | 1.3 | 29.4 |
|   |   | 250 | 44.5 | 65.4 | 1.8 | 1.2 | 29.1 |
|   |   | 600 | 25.6 | 65.6 | 1.5 | 1.1 | 16.8 |
| 9 | H | 10 | 47.2 | 39.8 | 3.9 | 2.8 | 18.8 |
|   |   | 30 | 47.0 | 39.9 | 3.8 | 2.8 | 18.8 |
|   |   | 50 | 47.0 | 40.0 | 3.5 | 2.7 | 18.8 |
|   |   | 250 | 46.7 | 40.3 | 3.2 | 2.5 | 18.8 |
|   |   | 600 | 24.6 | 49.3 | 2.3 | 2.4 | 12.1 |
| 10 | I | 10 | 72.4 | 21.3 | 16.4 | 2.5 | 15.4 |
|   |   | 250 | 71.5 | 22.4 | 14.8 | 2.1 | 16.0 |
| 11 | J | 10 | 14.5 | 64.5 | 9.7 | 2.4 | 9.35 |
|   |   | 250 | 13.7 | 63.8 | 9.6 | 2.1 | 8.74 |
| 12 | K | 10 | 26.5 | 43.1 | 8.2 | 2.2 | 11.4 |
|   |   | 250 | 25.9 | 44.6 | 7.6 | 1.7 | 11.6 |
| 13 | F | 10 | 80.0 | 35.6 | 17.5 | 1.3 | 28.5 |
|   |   | 250 | 78.9 | 36.5 | 16.2 | 1.2 | 28.8 |
| 14 | L | 5 | 46.7 | 55.6 | 1.2 | 0.2 | 26.0 |
|   |   | 250 | 45.4 | 56.1 | 1.1 | 0.2 | 25.5 |
| 15 | M | 5 | 66.9 | 50.1 | 3.4 | 1.1 | 33.5 |
|   |   | 10 | 66.8 | 50.2 | 3.4 | 1.1 | 33.5 |
|   |   | 30 | 66.2 | 50.5 | 3.4 | 1.1 | 33.4 |
|   |   | 50 | 65.9 | 50.8 | 3.3 | 1.0 | 33.5 |
|   |   | 250 | 64.5 | 51.2 | 3.1 | 0.9 | 33.0 |
| 16 | N | 5 | 61.2 | 47.1 | 0.6 | 1.5 | 28.8 |
|   |   | 250 | 59.2 | 48.4 | 0.7 | 1.4 | 28.7 |
| 17 | A | 10 | 71.8 | 38.1 | 5.0 | 1.9 | 27.4 |
|   |   | 250 | 71.4 | 39.3 | 4.2 | 1.5 | 28.1 |
| 18 | A | 10 | 71.5 | 38.2 | 5.3 | 2.0 | 27.3 |
|   |   | 250 | 71.0 | 39.4 | 4.0 | 1.6 | 28.0 |
| Comparative Example | | | | | | | |
| 1 | E | 10 | 72.2 | 36.5 | 9.7 | 2.4 | 26.4 |
|   |   | 30 | 71.1 | 37.1 | 9.5 | 2.3 | 26.4 |
|   |   | 50 | 1.9 | 3.7 | 0.5 | 0.0 | 0.07 |
| 2 | H | 10 | 44.3 | 38.7 | 3.7 | 2.8 | 17.1 |
|   |   | 30 | 43.9 | 39.1 | 3.5 | 2.7 | 17.2 |
|   |   | 50 | 1.2 | 2.1 | 0.0 | 0.0 | 0.03 |
| 3 | F | 30 | 43.9 | 65.1 | 2.5 | 1.4 | 28.6 |
|   |   | 50 | 0.2 | 1.2 | 0.0 | 0.0 | 0.002 |
| 4 | M | 5 | 65.1 | 49.0 | 3.1 | 1.2 | 31.9 |
|   |   | 10 | 0.5 | 1.8 | 0.0 | 0.0 | 0.009 |
| 5 | O | 5 | 17.3 | 0.0 | 0.7 | 0.0 | 0.0 |
|   |   | 10 | 5.5 | 0.0 | 0.2 | 0.0 | 0.0 |
| 6 | O | 5 | 17.6 | 0.0 | 0.6 | 0.0 | 0.0 |
|   |   | 10 | 8.2 | 0.0 | 0.3 | 0.0 | 0.0 |
| 7 | P | 5 | 25.0 | 0.1 | 0.0 | 0.0 | 0.03 |
|   |   | 10 | 8.6 | 0.6 | 0.0 | 0.0 | 0.05 |
| 8 | Q | 5 | 25.4 | 0.0 | 0.0 | 0.0 | 0.0 |
|   |   | 10 | 5.3 | 0.0 | 0.0 | 0.0 | 0.0 |

What is claimed is:

1. A process for producing iodotrifluoromethane, comprising reacting trifluoromethane with iodine in the presence of oxygen by use of a catalyst containing a salt of an alkali metal, an alkaline earth metal or combinations thereof, supported by a carbonaceous carrier, wherein the oxygen is fed in a volume ratio to the trifluoromethane (oxygen/trifluoromethane) ranging from 0.01 to 1.0.

2. The process for producing iodotrifluoromethane according to claim 1, wherein the salt of the alkali metal or the alkaline earth metal is used in combination with a salt of a noble metal.

3. The process for producing iodotrifluoromethane according to claim 2, wherein the alkali metal is at least one selected from the group consisting of potassium, rubidium, and cesium, the alkaline earth metal is at least one selected from the group consisting of magnesium, barium, and calcium, and the noble metal is at least one selected from the group consisting of platinum, ruthenium, rhodium, palladium, and iridium.

4. The process for producing iodotrifluoromethane according to claim 3, wherein the alkali metal is potassium and cesium in conbination, or potassium and rubidium in conbination, and the noble metal is platinum.

5. The process for producing iodotrifluoromethane according to claim 1, wherein the carbonaceous carrier is at least one selected from the group consisting of active carbon, graphite, fibrous active carbon, and carbon molecular sieves.

6. The process for producing iodotrifluoromethane according to claim 1, wherein unreacted iodine is recovered as a high-purity molecular iodine, and is recycled.

* * * * *